United States Patent [19]
Kossmann et al.

[11] Patent Number: 6,162,966
[45] Date of Patent: Dec. 19, 2000

[54] MODIFIED STARCH FROM PLANTS, PLANTS SYNTHESIZING THIS STARCH, AND PROCESSES FOR ITS PREPARATION

[76] Inventors: Jens Kossmann, Golmer Fichten 9, Golm 14476; Franziska Springer, Mühlenstr. 1, Berlin 14167; Volker Büttcher, Hundebreite 39, Lauenförde 37697, all of Germany

[21] Appl. No.: 08/913,671

[22] PCT Filed: Mar. 8, 1996

[86] PCT No.: PCT/EP96/01007

§ 371 Date: Feb. 2, 1998

§ 102(e) Date: Feb. 2, 1998

[87] PCT Pub. No.: WO96/27674

PCT Pub. Date: Sep. 12, 1996

[30] Foreign Application Priority Data

Mar. 8, 1995 [DE] Germany .............................. 195 09 695

[51] Int. Cl.⁷ .............................. A01H 5/00; A01H 5/06; C12N 15/29; C12N 15/82
[52] U.S. Cl. ..................... 800/284; 800/286; 800/317.2; 435/101; 435/193; 435/419; 435/468; 536/23.6
[58] Field of Search ...................... 800/284, 286, 800/298, 317.2; 435/419, 468, 193, 101; 536/23.6

[56] References Cited

FOREIGN PATENT DOCUMENTS

WO 92/14827  9/1992  WIPO .
WO 95/07355  3/1995  WIPO .............................. C12N 15/54

OTHER PUBLICATIONS

Hart et al. Mol. Gen. Genet. 235: 179–188, 1992.
Mazzolini et al. Plant Mol. Biol. 20: 715–731, 1992.
Evans et al. Biochem. Soc. Trans. 20: 3445, 1992.
Kossmann et al. Progress in Biotechnol. 10: 271–278, 1995.
Muller–Rober, B., and J. Kossmann, "Approaches to Influence Starch Quantity and Starch Quality in Transgenic Plants," *Plant, Cell And Environment* 17:601–613 (1994).
Takaha, T., et al., "Disproportionating Enzyme (4–α Glucanotransferase; EC 2.4.1.25) of Potato: Purification, Molecular Cloning, and Potential Role in Starch Metabolism," *J. Biol. Chem.* 268:1391–1396 (1993).
WPI Database, Section Ch, Week 8839, Derwent Publications Ltd., London, GB; Class D17, AN 88–275344 XP002005944 & JP63202396 A (Ezaki Glico), "Oligosaccharide production—containing N–acetyl glucosamine, glucosamine, mannose, or allose at terminal," Aug. 22, 1988.

*Primary Examiner*—David T. Fox
*Attorney, Agent, or Firm*—Fish & Neave; James F. Haley, Jr.; Elinor K. Shin

[57] ABSTRACT

The present invention describes transgenic plant cells and plants which due to a reduced activity of a disproportionating enzyme (D enzyme) synthesize a modified starch. Furthermore, the starch synthesized in these plant cells and plants is described.

9 Claims, 3 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(iii) HYPOTHETICAL: YES (iv) ANTI-SENSE: NO (xi) SEQUENCE DESCRIPTION: SEQ ID NO: 1:

GCCCCCGGGC TTTTAAGTTC CTTG                                          24

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(iii) HYPOTHETICAL: YES (iv) ANTI-SENSE: NO (xi) SEQUENCE DESCRIPTION: SEQ ID NO: 2:

CAGGGTACCT AACATCTTAA TCATC                                         25

MODIFIED STARCH FROM PLANTS, PLANTS SYNTHESIZING THIS STARCH, AND PROCESSES FOR ITS PREPARATION

This application is filed under 35 U.S.C. § 371 as a national stage application of the International application PCT/EP96/01007, filed Mar. 8, 1996, and is entitled to priority under 35 U.S.C. § 119 to German patent application 195 09 695.9, filed Mar. 8, 1995.

BACKGROUND OF THE INVENTION

The present invention relates to transgenic plants which due to genetically engineered modifications synthesize a modified starch, particularly a starch that possesses modified pastification properties and an increased phosphate content as compared to starch synthesized in wild-type plants. Furthermore, the invention relates to processes for producing said transgenic plants as well as the modified starch isolatable from these plants. The invention also relates to the use of DNA sequences encoding disproportionating enzymes (EC 2.4.1.25) for the production of transgenic plants exhibiting a reduced activity of said enzymes and synthesizing a modified starch.

The polysaccharide starch which represents one of the main storage substances in the plant kingdom, in addition to its use in the food stuff industry is also widely used as regenerative source of raw materials for the production of industrial products. In order to facilitate the use of this raw material in as many areas as possible, it is important to obtain a large variety of substances and to adapt it to the respective demands of the manufacturing industry.

Although starch is made up of a chemically homogeneous basic component, namely the glucose, it does not represent a homogeneous raw material. Rather, it constitutes a highly complex mixture from various types of molecules which differ from each other in their branching degree and in the occurrence of the branchings of the glucose chains. One differentiates particularly between amylose-starch, a basically non-branched polymer made up of α-1,4-interlinked glucose molecules, and amylopectin-starch which in turn is a mixture of glucose chains with different branching degree. The branching results from α-1,6-glycosidic interlinkings.

The molecular structure of starch which is mainly determined by the branching degree, the amyloselamylopectin ratio, the average chain length as well as the presence of phosphate groups, is decisive for essential functional properties of the starch or the aqueous solutions thereof. Examples of essential functional properties are solubility, retrogradation behavior, the film forming properties, the viscosity, the color stability, the pastification properties, i.e., binding and adhesive properties, as well as low temperature stability. Also the starch granule size may be important for various uses.

The starch isolated from plants is often adapted to industrial uses by chemical modification, which, as a rule, is time and cost intensive. Therefore it appears to be desirable to find possibilities of synthesizing modified starch, which in its properties already meets the demands of the manufacturing industry, directly in plants and isolating the modified starch from these plants. Conventional means for producing plants synthesizing starch that is modified as compared to that produced in wild-type plants are the classical breeding methods and the generation of mutants. For example, in maize a mutant was generated that synthesizes a starch having modified viscosity properties (U.S. Pat. No. 5,331, 108) as well as a maize variety (waxy maize) was established by breeding the starch of which consists by almost 100% of amylopectin (Akasuka and Nelson, J. Biol. Chem. 241 (1966), 2280–2285).

Alternatively, plants synthesizing a starch with modified properties can be produced by genetic engineering. Described are, for example, several cases where potato plants were genetically modified with the aim of modifying the starch synthesized in these plants (e.g., WO 92/11376; WO 92/14827). Although in some cases the production of a modified starch in plants was successful, there is still the need for processes for the production of a starch which is modified as compared to starch synthesized in wild-type plants and which is preferably useful in specific industrial manufacturing processes.

The problem underlying the present invention therefore is to provide plants synthesizing a modified starch which differs in its physical and chemical properties from starch naturally synthesized in plants and which thus is more useful for specific purposes, as well as processes for producing such plants.

The problem is solved by the provision of the embodiments characterized in the claims.

SUMMARY OF THE INVENTION

Thus, the present invention relates to transgenic plant cells in which the activity of a "disproportionating enzyme" (also 4-α-glucanotransferase; EC 2.4.1.25; referred to hereinafter as D enzyme) is reduced as compared to non-transformed cells, either due to the introduction and expression of an exogenous DNA sequence or the introduction of a mutation into a gene encoding a disproportionating enzyme.

It has been surprisingly found that transgenic plants containing such cells and exhibiting a reduced activity of the D enzyme as compared to wild-type plants synthesize a modified starch which strongly differs in its physical and chemical properties from starch naturally synthesized in plants. Aqueous solutions of the starch synthesized in these plants, for example, exhibit a clearly modified viscosity behavior as compared to starch synthesized in wild-type plants. A reduced activity of the D enzyme as compared to wild-type plants means that these plants exhibit only 50%, preferably less than 25% and most preferably less than 10% of the D enzyme activity of wild-type plants.

D enzymes are defined as enzymes catalyzing the transfer of glucans from a 1,4-α-D glucan to another 1,4-α-D glucan or to glucose. Effective glucan donors are maltooligosaccharids, soluble starch, as well as amylopectin (Takaha et al., J. Biol. Chem. 268 (1993), 1391–1396). As a rule, a maltose group is transferred unless maltotetraose is the donor. In this case, maltotriose is transferred.

"Exogenous DNA sequence" means that the DNA sequence introduced is either heterologous with respect to the transformed plant cell, i.e., is derived from a cell with a different genetic background, or homologous with respect to the transformed cell but in this case is not localized in its natural surroundings in the genome of the transformed cell. This means that the exogenous DNA sequence is localizes at a position in the genome where it does not naturally occur and that it is flanked by genes which are not naturally adjacent to it.

"Expression" means that the exogenous DNA sequence is at least transcribed in the cells. If it encodes a protein, this term also comprises translation.

The reducton of the D enzyme activity in cells according to the invention can basically be brought about in various manners.

In a preferred embodiment, the reduction of the D enzyme activity in the transgenic cells is achieved by inhibition of the synthesis of a functional D enzyme in the cells.

"Inhibition of the synthesis" means that the synthesis of an endogenous D enzyme is reduced in comparison to nontransformed cells, preferably by at least 50%, particularly by at least 75% and most preferably by at least 90%. The reduction of the synthesis can be detected by, e.g., detection of the enzyme in a Western blot analysis using D enzyme-specific antibodies. The D enzyme activity can furthermore be detected as described by Takaha et al. (J. Biol. Chem. 268 (1993), 1391–1396). The D enzyme transcripts can also be detected by Northern blot analysis.

"Functional" means that the enzyme exhibits its natural enzyme activity described above and that this activity is about as high as that in wild-type cells.

A reduction of the synthesis of a D enzyme in the cells according to the invention can be brought about in various manners. A first possibility is to modify the endogenous D enzymes encoding sequences which are present in the genome of the cell or the regulatory regions thereof.

They can be inactivated by, e.g., transposon mutagenesis, other conventional mutagenesis methods or "gene tagging", thereby largely or completely inhibiting the synthesis of endogenous D enzymes.

Possibilities of modifying the genomic sequences include, e.g., gene disruption, insertion, deletion, recombination, addition, etc.

Besides a complete inactivation of the genomic DNA sequences encoding D enzymes it is also conceivable to modify them such that no functional D enzyme is synthesized in the cells any longer.

Another possibility is to disrupt the transcription or translation of the genes for D enzymes being present in the cell in endogenous form. Techniques for doing so are known in the art.

In a preferred embodiment, the reduction of the synthesis of the functional D enzyme takes place in the cells according to the invention by way of an antisense effect.

In another preferred embodiment, the reduction of the synthesis of the functional D enzyme takes place in the cells according to the invention by way of expression of a ribozyme which specifically cleaves transcripts encoding the D enzyme. Particularly preferred are ribozymes which are combined with sequences bringing about an antisense effect, i.e., which are complementary to D enzyme transcripts.

Another possibility of reducing the synthesis of the functional D enzyme is to make use of a cosuppression effect.

Another possibility of reducing the D enzyme activity in plant cells consists in the inactivation of already synthesized D enzymes.

In a preferred embodiment, the exogenous DNA sequence encodes a polypeptide which brings about the reduction of the D enzyme activity. Conceivable is here, e.g., the expression of D enzyme specific antibodies.

If the exogenous DNA sequence shall be expressed in the transgenic cells, it is linked with regulatory elements which allow transcription in plant cells. Examples of such elements are, e.g., promoters. In principle, any promoter that is active in plant cells can be used for the expression. The promoters may be viral as well as plant promoters. The promoter may be homologous or heterologous with respect to the plant species used as well as with respect to the exogenous DNA sequence. Suitable are both promoters allowing a constitutive expression, such as the 35S promoter of the cauliflower mosaic virus (Odell et al., Nature 313 (1985), 810–812) and the promoter construct described in WO94/01571 as well as promoters that lead to expression of subsequent sequences only at a certain point of time determined by external factors (see, e.g., WO93/07279) or in a certain tissue of the plant (see, e.g., Stockhaus et al., EMBO J. 8 (1989), 2245–2251). Preferably, promoters are used that are active in the typical "sink" organs of plants. "Sink" tissues are defined as net importers of the carbon dioxide bound in photosynthetically active tissues. Typical sink organs are, e.g., roots, flowers and storage organs. In the process according to the invention, preferably promoters are used that are active in the starch-storing organs of the plants to be transformed. Possible starch-storing organs are, e.g., the seeds of various cereals, maize, rice, and peas, as well as the tubers of potatoes. Known are, e.g., the USP promoter from *Vicia faba* which allows a seed-specific expression in *Vicia faba* as well as in other plant species (Fiedler et al., Plant Mol. Biol. 22 (1993), 669–679; Bäumlein et al., Mol. Gen. Genet. 225 (1991), 459–467) as well as the promoter of the acyl carrier protein gene (Baerson et al., Plant Mol. Biol. 22 (1993), 255–267). Promoters which are known to be active in the endospermium of grains of maize are, e.g., the promoters of the zein genes (Pedersen et al., Cell 29 (1982), 1015–1026; Quattrocchio et al., Plant Mol. Biol. 15 (1990), 81–93). For transformation of potatoes, the promoters of the patatin class I genes from potato may be particularly, but not exclusively, used which allow tuber-specific expression, such as the B33 promoter (Rocha-Sosa et al., EMBO J. 8 (1989), 23–29).

In addition to the promoter the regulatory elements may also contain DNA sequences allowing a still further reduction of the transcription, e.g., so-called enhancer elements. Such regions may be obtained from viral genes or suitable eukaryotic genes, or may be produced synthetically. They may be homologous or heterologous with respect to the promoter used.

If the exogenous DNA sequence encodes a polypeptide, it may further be linked with sequences being in the transcribed region and allowing a more efficient translation of the synthesized RNA into the respective protein, e.g., with so-called translation enhancers.

The regulatory elements may further comprise sequences which serve to correctly terminate the transcription or add a poly-A tail to the transcript which is said to have a function in the stabilization of the transcripts. Such elements are described in the literature and are freely exchangeable. Examples of such termination sequences are the 3'-nontranslated regions comprising the polyadenylation signal of the nopalin synthase gene (NOS gene) or of the octopin synthase gene (Gielen et al., EMBO J. 8 (1989), 23–29) from Agrobacteria, or the 3'-nontranslated regions of the genes of the storage proteins from soy bean, as well as the genes of the small subunit of the ribulose-1,5-bisphosphate carboxylas (ssRUBISCO).

If an antisense RNA is expressed to reduce the synthesis of the functional D enzyme, the exogenous DNA sequence encoding said RNA may in principle be any DNA sequence encoding a D enzyme and exhibiting sufficiently high homology in order to bring about an antisense effect in the cells. Preferably, DNA sequences from plants are used. The DNA sequence used preferably is of homologous origin with respect to the plant species to be transformed. However, DNA sequences from other species may also be used as long as it is guaranteed that the homology to the endogenous DNA sequences of the species to be transformed is sufficiently high so as to allow an antisense effect. The homology should be more than 80%, preferably more than 90% and most preferred more than 95%.

Sequences with a minimum length of 15 bp may be used. An inhibiting effect, however, is not excluded even if shorter sequences are used. Preferably, longer sequences with a length of 100 to 500 base pairs are used. For an efficient antisense inhibition, particularly sequences with a length of over 500 base pairs are used. As a rule, sequences are used which are shorter than 5,000 base pairs, preferably sequences that are shorter than 2,500 base pairs.

In a preferred embodiment, the cells according to the invention are transgenic potato cells which are transformed with a DNA sequence from potato encoding the D enzyme, or with part of such a sequence, particularly with parts of the DNA sequence described by Takaha et al. (J. Biol. Chem. 268 (1993, 1391–1396) (accessible in the GenEMBL data bank under accession no. X68664).

It is, however, possible to use other DNA sequences encoding D enzymes and being isolatable from other organisms, particularly from other plant species, e.g., by way of the already known sequences via hybridization and other standard techniques.

There are various possibilities for the inhibition of the synthesis of D enzymes in the cells of transgenic plants using a suitable ribozyme.

Ribozymes are catalytically active RNA molecules capable of cleaving RNA molecules at specific target sequences. By way of gene technological methods it is possible to modify the specificity of ribozymes. There are various classes of ribozymes. For the practical application with the purpose of specifically cleaving the transcript of a certain gene, the representatives of two different groups of ribozymes are preferably used. The one group are the ribozymes assigned to the group I intron ribozymes. The second group are ribozymes that are characterized by the structural feature of a so-called "hammerhead" motif. The specific recognition of the target RNA molecule can be modified by modifying the sequences flanking said motif. These sequences determine via base pairing with sequences in the target molecule the site where the catalytic reaction and thus the cleavage of the target molecule takes place. Since the sequence requirements for an efficient cleavage are extremely few, it appears to be possible in principle to develop specific ribozymes for virtually any RNA molecule. The production of genetically modified plant cells whose D enzyme activity is reduced may therefore also be brought about by introduction and expression of a recombinant double-stranded DNA molecule in plants, which is composed of (a) a promoter functional in plants, (b) a DNA sequence encoding a catalytic domain of a ribozyme and being flanked by DNA sequences which are homologous to sequences of the target molecule, and, (c) if necessary, a signal functional in plants for transcription termination and polyadenylation of an RNA molecule.

The sequence mentioned under (b) may encode, e.g., the catalytic domain of the satellite DNA of the SCMo virus (Davies et al., Virology 177 (1990), 216–224) or that of the satellite DNA of the TobR virus (Steinecke et al., EMBO J. 11 (1992), 1525–1530; Haseloff and Gerlach, Nature 334 (1988), 585–591).

The DNA sequences flanking the catalytic domain are composed of DNA sequences which are homologous to the sequences of endogenous D enzyme genes.

The transgenic plant cells according to the invention may in principle be derived from any plant species, particularly from plants expressing a protein having D enzyme activity. Both monocotyledonous as well as dicotyledonous plants are of interest. Preferably, the process is applied to useful plants, particularly to plants synthesizing starch as storage substance and forming starch-storing organs such as cereals, rice, potatoes, Leguminosae or cassava.

By cereals particularly monocotyledonous plants belonging to the order Poales, preferably those of the family of Poaceae are to be understood. Examples of such plants are plants belonging to the genera Avena (oats), Triticum (wheat), Secale (rye), Hordeum (barley), Oryza (rice), Panicum, Pennisetum, Setaria, Sorghum (millet), Zea (maize) etc. Examples of starch-storing Leguminosae are some species of the genera Pisum (e.g., *Pisum sativum*), Vicia (e.g., *Vicia faba*), Cicer (e.g., *Cicer arietinum*), Lens (e.g., *Lens culinaris*), Phaseolus (e.g., *Phaseolus vulgaris* and *Phaseolus coccineus*), etc.

For the production of expression cassettes allowing in the plant cells the synthesis of a polypeptide, an antisense RNA or a ribozyme etc., there is a large number of cloning vectors available which contain a replication signal for *E. coli* and a marker gene for selecting transformed bacterial cells. Examples of such vectors are pBR322, pUC series, M13mp series, pACYC184, etc. Conventional cloning methods are frequently described in the literature (see, e.g., Sambrook et al., Molecular Cloning: A Laboratory Manual (1989), Cold Spring Harbor, N.Y., Cold Spring Harbor Laboratory Press).

For the introduction of the expression cassette into a plant host cell, there is a large number of techniques available. These techniques include the transformation of plant cells with T-DNA using *Agrobacterium tumefaciens* or *Agrobacterium rhizogenes* as means for transformation, the fusion of protoplasts, the injection, the electroporation of DNA, the introduction of DNA by way of the biolistic method as well as further possibilities.

The expression cassette described above is preferably introduced into the plant cells using plasmids, particularly plasmids suitable for the transformation of plant cells and allowing integration of the expression cassette into the plant genome. For injection and electroporation of DNA in plant cells, there are no specific requirements for the plasmids used. Simple plasmids such as pUC derivatives may be used. If, however, whole plants are to be regenerated from cells so transformed, the presence of a selectable marker gene is required.

Further DNA sequences may be required depending on the method of introduction into the plant cell. If, e.g., the Ti or Ri plasmid is used for the transformation of the plant cell, at least the right border, often, however, the right and left border of the Ti and Ri plasmid T-DNA has to be linked as flanking region to the genes to be introduced.

The infection of a plant cell then results in the incorporation of the T-DNA including the new genes into the chromosomes of the plant cell.

For the transformation using Agrobacteria, the DNA to be introduced has to be first cloned into special plasmids, e.g., into an intermediate or into a binary vector. The intermediate vector can be transferred to *Agrobacterium tumefaciens* by conjugation using a helper plasmid and can then be integrated into the Ti or Ri plasmid of Agrobacteria by homologous recombination due to sequences that are homologous to the sequences in the T-DNA. These plasmids additionally receive the vir region required for the transfer of the T-DNA.

In contrast to intermediate vectors that do not replicate in Agrobacteria, binary vectors are capable of replicating both in *E. coli* and in Agrobacteria. They possess a selection marker gene and a linker or polylinker which are flanked by the right and left T-DNA border region and can be transformed directly in Agrobacteria (Holsters et al., Mol. Gen. Genet. 163 (1978), 181–187). Known binary vectors are, e.g., the vector pBinAR (Höfgen and Willmitzer, Plant. Sci. 66 (1990), 221–230) or the vector pBin19 (Bevan, Nucl. Acids Res. 12 (1984), 8711–8721), which is commercially available (Clontech Laboratories, Inc., USA).

Intensive research work was done on the transfer of T-DNA including the new genes in plant cells and is sufficiently described in EP 120516; Hoekema, In: The Binary Plant Vector System Offsetdrukkerij Kanters B. V., Alblasserdam (1985), Chapter V; Fraley et al., Crit. Rev. Plant. Sci., 4 (1986), 1–46 and An et al., EMBO J. 4 (1985), 277–287.

For the transfer of the DNA into the plant cell, it is suitable to co-cultivate plant explants with *Agrobacterium tumefaciens* or *Agrobacterium rhizogenes*. From the infected plant material (for example leaf explants, segments of stems, roots but also protoplasts or suspension cultivated plant cells) whole plants can be regenerated in a suitable medium which may contain antibiotics or biozides for the selection of transformed cells. The plants obtained that way can then be examined for the presence of the introduced DNA.

While the transformation of dicotyledonous plants via Ti plasmid vector systems using *Agrobacterium tumefaciens* is a well-established method, more recent research has shown that monocotyledonous plants, too, may very well be transformed by way of Agrobacteria-based vectors (Chan et al., Plant Mol. Biol. 22 (1993), 491–506; Hiei et al., Plant J. 6 (1994), 271–282; Deng et al., Science in China 33 (1990), 28–34; Wilmink et al., Plant Cell Reports 11 (1992), 76–80; May et al., Bio/Technology 13 (1995), 486–492; Conner and Domisse, Int. J. Plant Sci. 153 (1992) 550–555; Ritchie et al., Transgenic Res. 2 (1993), 252–265).

Alternative systems for the transformation of monocotyledonous plants are the transformation via the biolistic approach (Wan and Lemaux, Plant Physiol. 104 (1994), 37–48; Vasil et al., Bio/Technology 11 (1993), 1553–1558; Ritala et al., Plant Mol. Biol. 24 (1994), 317–325; Spencer et al., Theor. Appl. Genet. 79 (1990), 625–631), the protoplast transformation, the electroporation of partially permeabilized cells, the introduction of DNA using glass fibers.

Particularly, the transformation of maize is variously described in the literature (cf., e.g., WO95/06128, EP 0 513 849; EP 0 465 875; Fromm et al., Biotechnology 8 (1990), 833–844; Gordon-Kamm et al., Plant Cell 2 (1990), 603–618; Koziel et al., Biotechnology 11 (1993), 194–200). EP 292 435 describes a process by way of which fertile plants can be obtained starting from a mucus-less, friable, grenulaceous maize callus. Shillito et al. (Bio/Technology 7 (1989), 581) observed in this context that it is necessary for the regeneration to fertile plants to start from callus suspension cultures from which a culture of dividing protoplasts capable of regenerating to plants is producible. After an in vitro cultivation of 7 to 8 months Shillito et al. obtain plants with viable progeny which, however, exhibit abnormalities regarding morphology and reproductivity.

Prioli and Söndahl (Bio/Technology 7 (1989), 589) describe the regeneration and production of fertile plants from maize protoplasts of the Cateto maize inbred line Cat 100-1. The authors assume that the protoplast regeneration to fertile plants depends on a variety of factors, such as genotype, physiological condition of the donor cells and the cultivation conditions. The successful transformation of other cereal species has already been described, e.g., for barley (Wan and Lemaux, supra; Ritala et al., supra) and for wheat (Nehra et al., Plant J. 5 (1994), 285–297).

Once the introduced DNA has been integrated into the genome of the plant cell, it usually is stable there and is also contained in the progeny of the originally transformed cell. It usually contains a selection marker which makes the transformed plant cells resistant to a biozide or an antibiotic such as kanamycin, G 418, bleomycin, hygromycin or phosphinotricin and others. Therefore, the individually chosen marker should allow the selection of transformed cells from cells lacking the introduced DNA.

The transformed cells grow within the plant in the usual way (see also McCormick et al., Plan Cell Reports 5 (1986), 81–84). The resulting plants can be cultured normally and be cross-bred with plants possessing the same transformed genetic information or other genetic information. The hybrid individuals resulting therefrom possess the corresponding phenotype features.

Two or more generations should be cultivated to make sure that the phenotype feature is maintained stably and is transmitted. Seeds should be harvested to make sure that the corresponding phenotype or other properties are maintained.

A subject matter of the invention are plants containing the above-described transgenic plant cells according to the invention. Such plants may be regenerated from plant cells according to the invention by, e.g., microbiological processes such as described in the examples. The term "plant" also refers to parts of the plant, such as individual organs (leaves, root, stem), etc., harvestable parts, tissues, etc. Harvestable parts are, e.g., seeds, tubers, photosynthetic tissues, storage roots, etc.

The invention furthermore relates to the propagation material of the plants of the invention which contains the transgenic plant cells described above. Examples thereof are fruits, seeds, cuttings, root stocks, tubers, etc.

Due to the reduction of the activity of the D enzyme a modified starch is synthesized in the cells and plants according to the invention which differs with regard to its physical and chemical properties, particularly its pastification properties as well as its phosphate content from starch synthesized in wild-type plants.

Therefore, another subject matter of the invention is a starch obtainable from the cells, plants or propagation material of the plants according to the invention which exhibit a reduced D enzyme activity as compared to wild-type plants.

The starch obtainable from the plant cells and plants according to the invention in which the synthesis of the D enzyme is inhibited exhibits characteristics which widely vary from those of starch isolatable from wild-type plants, e.g., modified pastification properties. This variation manifests itself in a modified viscosity of aqueous solutions of said starch as compared to aqueous solutions from wild-type starch (see FIGS. 3, 4, 5 and 6).

A conventional test used to determine the viscosity properties is the so-called Brabender test. This test is carried out using an apparatus which is known, e.g., as Viskograph E. This apparatus is produced and sold inter alia by Brabender OHG Duisburg (Germany).

The test essentially consists of first heating starch in the presence of water in order to determine when the hydratization and the swelling of the starch granules begins. This process which is also referred to as gelatinization or pastification is brought about by the dissolution of hydrogen bonds and is correlated with a measurable increase in viscosity of the starch suspension. While a further temperature increase after gelatinization results in the complete dissolution of the starch particles and a decrease in viscosity, a temperature decrease directly after gelatinization will typically result in an increase in viscosity (see FIG. 6). The result of the Brabender test is a curve which shows the viscosity in dependence on time, wherein first a temperature increase beyond the gelatinization temperature can be observed and then a cooling off.

As a rule, the analysis of the Brabender curve serves to determine the pastification temperature, the maximum viscosity during heating, the viscosity after prolonged boiling, the increase in viscosity during cooling and the viscosity after cooling down. These parameters represent important characteristics which determine the quality of a starch as well as its usefulness for various applications. Furthermore, the starch obtainable from the plant cells and plants according to the invention with a reduced D enzyme activity exhibits an increase phosphate content as compared to starch from wild-type plants, particularly a phosphate content that is by at least 10% higher, preferably by 20% higher than the phosphate content of starch of wild-type plants.

The term "modified starch" in this invention is understood to refer to a starch which differs from wild-type starch with respect to its physical and chemical properties, particularly a starch which exhibits modified pastification properties as compared to wild-type starch and the aqueous solutions of which exhibit a modified viscosity as compared to aqueous solutions of wild-type starch. The viscosity is preferably measured with a Brabender Viskograph. Furthermore, a starch modified in that manner will display an increase in phosphate content as compared to wild-type starch. The phosphate content of said starch is by at least 10%, preferably by 20% and most preferably by 30% higher than the phosphate content of wild-type starch.

A starch modified in that manner, which is the subject matter of the present invention, preferably exhibits the characteristic Brabender curves shown in FIGS. 3, 4 and 5. The modified starch under the conditions mentioned in Example 4 for determining the viscosity with a Brabender Viskograph particularly displays at least one of the following characteristic values or a combination of these values:

a pastification temperature of 67.3±0.0° C., a maximum viscosity of 2823.7±82.0 BU a viscosity at the start of the holding time of 1517.3±62.3 BU a viscosity at the start of the cooling time of 641.3±19.7 BU a viscosity after cooling down of 998.0±18.3 BU.

Within the limits of measuring accuracy, these mean values may deviate downwards or upwards by up to 10% from the values mentioned so that the afore-mentioned characteristic values for the modified starch may assume the following values:

a pastification temperature of 67.3±6.7° C., a maximum viscosity of 2824±283 BU a viscosity at the start of the holding time of 1517.3±152 BU a viscosity at the start of the cooling time of 641±65 BU a viscosity after cooling down of 998±100 BU.

The modified starch usually displays at least one of the characteristic values mentioned above, preferably a combination of more than one of these values. Most preferably, all values are within the indicated ranges.

By applying the antisense technology it is furthermore possible to produce plants in which the expression of DNA sequences encoding D enzymes is inhibited to a varying extent and that therefore display an activity of the D enzyme that is reduced to varying degrees. Depending on the degree of reduction of the D enzyme activity such transgenic plants synthesize starch which differs to a larger or smaller extent from starch obtained from wild-type plants in terms of their pastification behavior and their phosphate content.

In general, starches modified in that manner display the following properties as compared to starch from wild-type plants:

1. a higher maximum viscosity during heating 2. a higher viscosity after cooling down.

The starch is isolated according to conventional methods, such as described in "Handbuch der Stärke" (Vol. I, Max Ullmann (ed.), 1974, Paul Parey Verlag, Berlin, Germany) or in Morrison and Karkalas (Methods in Plant Biochemistry, 2 (1990), 323–352, Academic Press Ltd., London).

The starches of the invention may be modified according to techniques known to the skilled person; in unmodified as well as in modified form they are suitable for various uses in foodstuffs and in non-foodstuffs.

Basically, the possibilities of uses of the starch can be subdivided into two major fields. One field comprises the hydrolysis products of starch, essentially glucose and glucans components obtained by enzymatic or chemical processes. They can be used as starting material for further chemical modifications and processes, such as fermentation. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g., increasing the surface of the grain, improved digestibility due to less branching or a steric structure, which limits the accessibility for the used enzymes.

The other field in which the starch is used because of its polymer structure as so-called native starch, can be subdivided into two further areas:

1. Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with, e.g., inorganic or organic ions.

2. Use in Non-Foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

2.1 Paper and Cardboard Industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textile and Textile Care Industry

Another possible use of the starches as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building Industry

The fourth area of application of starch is its use as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilization

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use of Starch in Plant Protectives and Fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, Medicine and Cosmetics Industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an Additive in Coal and Briquettes

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

2.9 Processsing of Ore and Coal Slurry

Furthermore, the starch may be used as a flocculant in the processing of ore and coal slurry.

2.10 Starch as an Additive in Casting

Another field of application is the use as an additive to process materials in casting. For various casting processes, cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Use of Starch in Rubber Industry

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of Leather Substitutes

Another field of application for the modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved anti-block behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced using a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. In the last few years, these super absorbers have been used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically engineering a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art. These are particularly modifications by means of heat treatment acid treatment oxidation and esterifications, leading to the formation of phosphate, nitrate, sulfate, xanthate, acetate and citrate starches. Other organic acids may also be used for the esterification:

formation of starch ethers starch alkyl ether, O-allyl ether, hydroxylalkyl ether, O-carboxylmethyl ether, N-containing starch ethers, P-containing starch ethers and S-containing starch ethers.

formation of cross-linked starches formation of starch graft polymers.

The invention thus also relates to the use of the starches according to the invention for the production of food-stuffs or industrial products.

Furthermore, the present invention relates to the use of DNA sequences encoding enzymes with the enzymatic activity of a D enzyme for the genetic engineering of plants in order to produce plants synthesizing a starch which is modified as compared to wild-type starch.

The plasmids produced and used within the present invention were deposited with Deutsche Sammlung von Mikroorganismen (DSM) [German collection of microorganisms] in Brunswick, Federal Republic of Germany, as international recognized depositary authority in accordance with the stipulations of the Budapest Treaty on the International Recognition of the Deposit of Microorganisms for the Purposes of Patent Procedure.

On Aug. 26 1993 following plasmid was deposited with Deutsche Sammlung von Mikroorganismen (DSM) in Brunswick, Germany (deposit no.):

Plasmid p35SH-anti-D (DSM 8479)

On Aug. 10, 1994 following plasmid was deposited with Deutsche Sammlung von Mikroorganismen (DSM) in Brunswick, Germany (deposit no.):

Plasmid p35S-anti-D (DSM 9365)

Furthermore, on Oct. 20, 1994 following plasmid was deposited with the above-mentioned depositary authority (deposit no.):

Plasmid pBinAR-Hyg (DSM 9505)

The plasmid contains the following fragments:

A = Fragment A (529 bp) comprises the 35S promoter of the cauliflower mosaic virus (CaMV); nucleotides 6906–7437 of the CaMV.

B = Fragment B (2909 bp) comprises a DNA fragment including the coding region for the disproportionating enzyme from potato (Takaha et al., J. Biol. Chem. 268 (1993), 1391–1396; nucleotides 303 to 1777) and being linked to the promoter in antisense orientation.

C = Fragment C (192 bp) comprises the polyadenylation signal of gene 3 of the T-DNA of the Ti plasmid pTiACH5, nucleotides 11749–11939.

The plasmid is about 12.7 kb in length and allows selection for hygromycin resistance in transformed plant cells.

Figure 2:
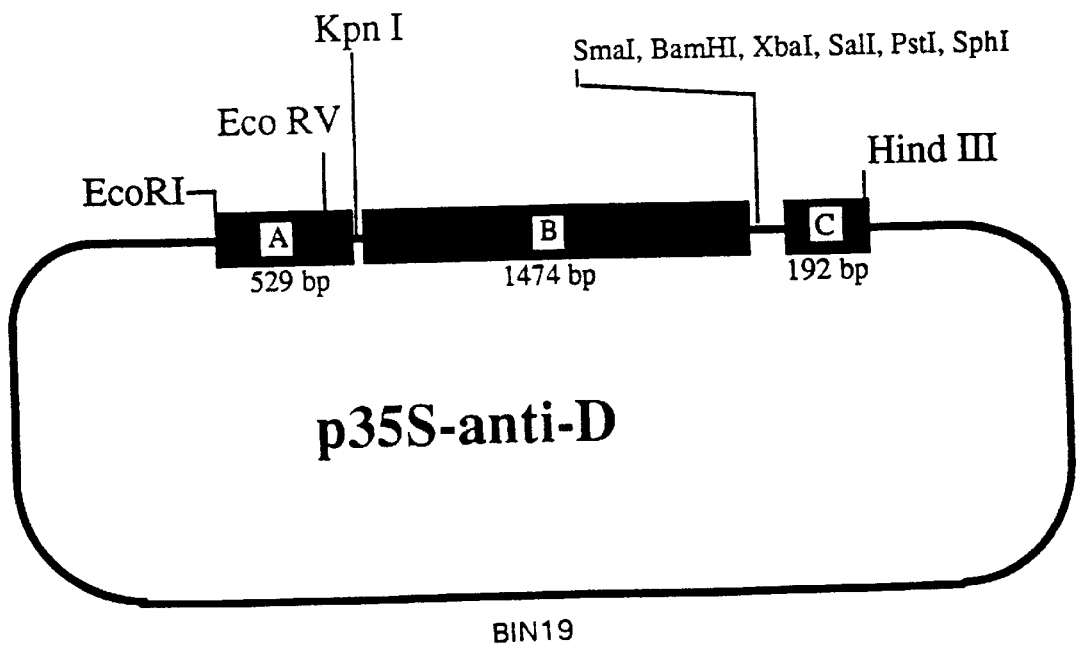

FIG. 2 shows plasmid p35S-anti-D (DSM 9365).

The plasmid contains the following fragments:

A = Fragment A (529 bp) comprises the 35S promoter of the cauliflower mosaic virus (CaMV); nucleotides 6906–7437 of the CaMV.

B = Fragment B (2909 bp) comprises a DNA fragment including the coding region for the disproportionating enzyme from potato (Takaha et al., J. Biol. Chem. 268 (1993), 1391–1396; nucleotides 303 to 1777) and being linked to the promoter in antisense orientation.

C = Fragment C (192 bp) comprises the polyadenylation signal of gene 3 of the T-DNA of the Ti plasmid pTiACH5, nucleotides 11749–11939.

The plasmid is about 12.2 kb in length and allows selection for kanamycin resistance in transformed plant cells.

Figure 3:
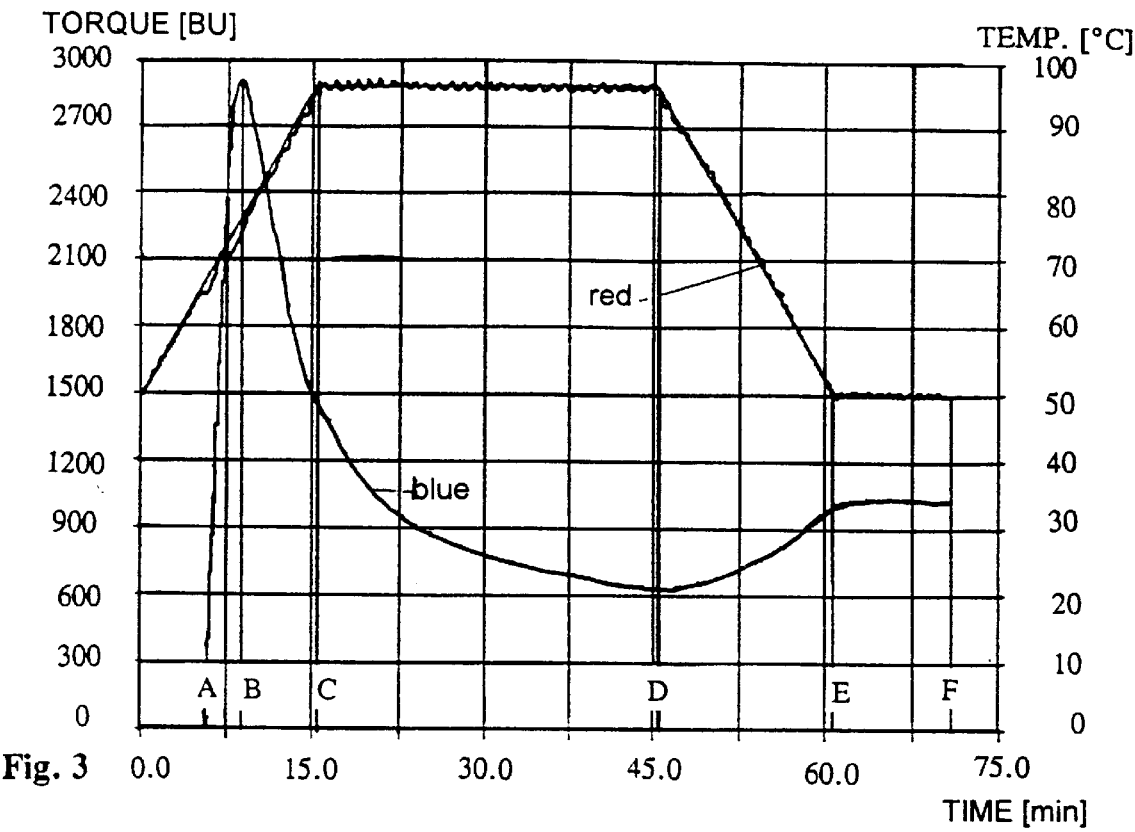

FIG. 3 shows a Brabender curve for an aqueous solution of starch from the transgenic potato line JD1-32. The curve was determined as explained in Example 3.

The following terms mean:

Tor torque
[BU] Brabender unit
Temp. temperature
A start of pastification
B maximum viscosity
C start of holding time
D start of cooling time
E end of cooling time
F end of final holding time The blue line indicates the viscosity (measured in Brabender units). The red line indicates the temperature profile.

Measurement Conditions:

Apparatus: Brabender Viskograph E (Brabender OHG Duisburg, Germany)
Amount of starch used: 30 g
Volume of solvent used: 450 ml distilled water
Stirring rate: 75 revolutions per minute
Heating: from 50° C. to 96° C. at a rate of 3° C. per minute
Holding the temperature: 30 min at 96° C.
Cooling: from 96° C. to 50° C. at a rate of 3° C. per minute.

Figure 4:
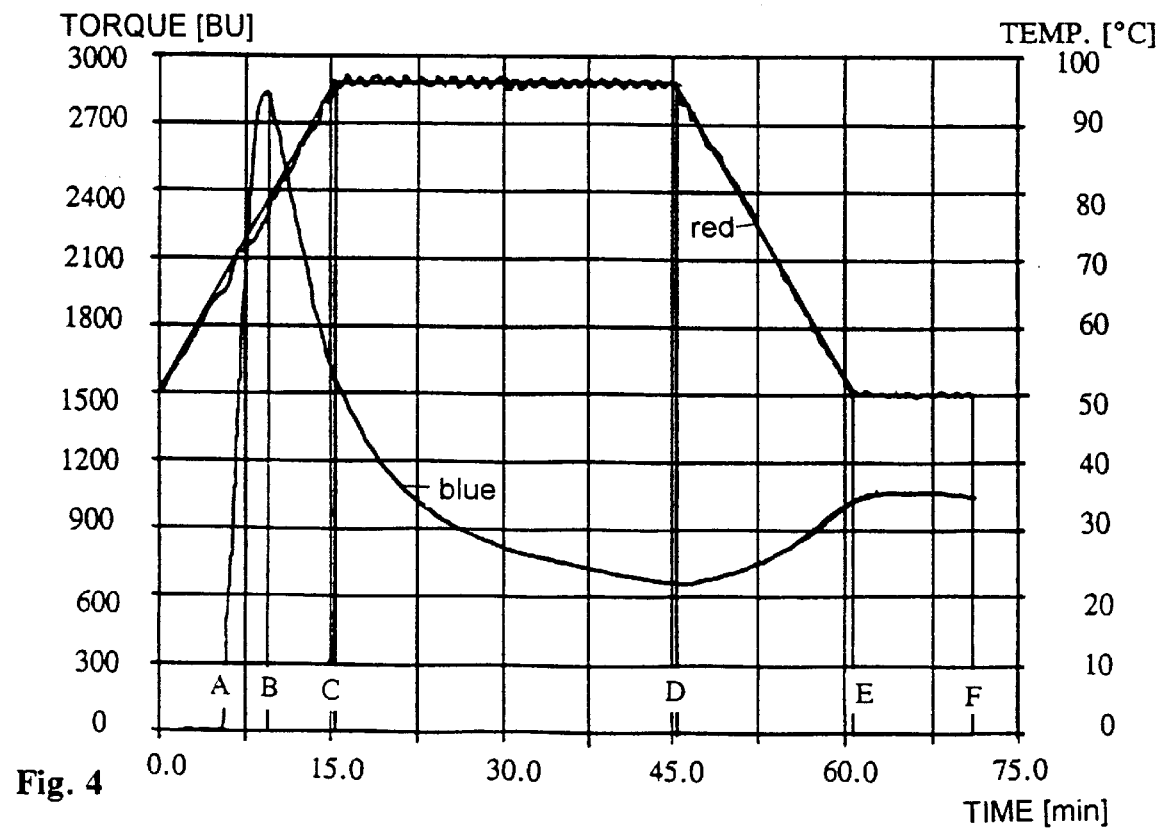

FIG. 4 shows a Brabender curve for an aqueous starch solution from the transgenic potato line JD1-33. The curve was determined as explained in Example 3.

The abbreviations are as defined for FIG. 3. The measurement conditions correspond to those described for FIG. 3.

Figure 5:
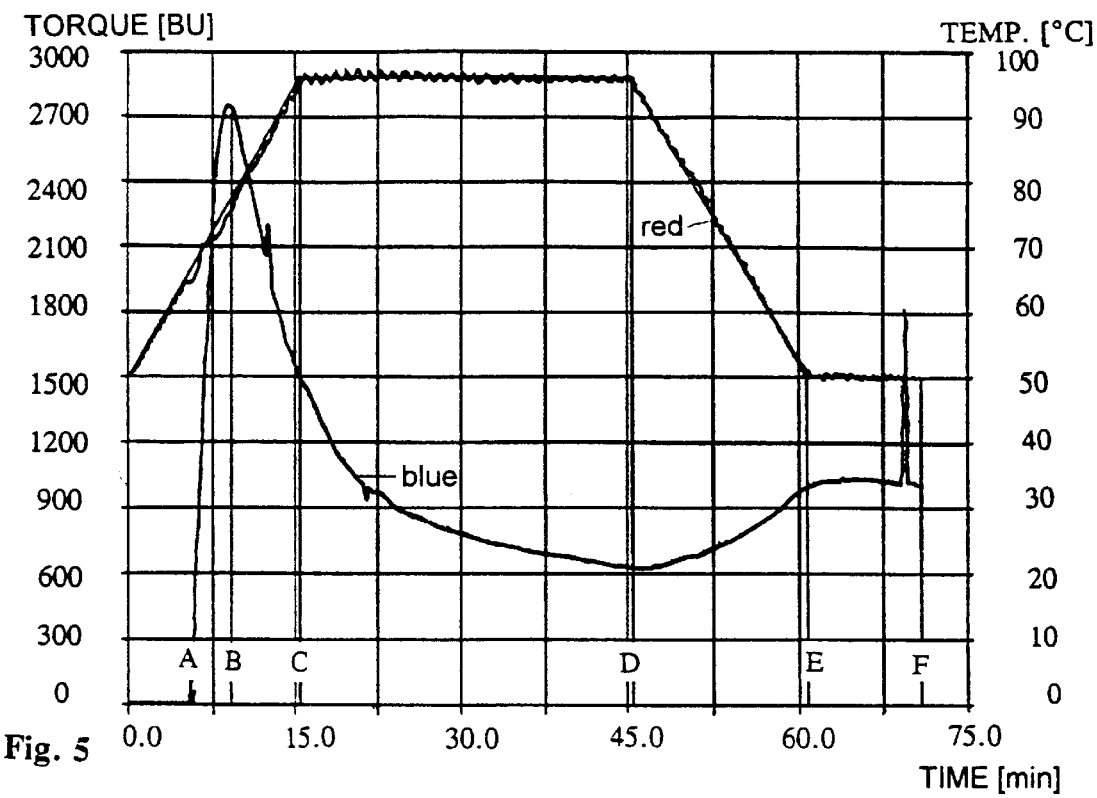

FIG. 5 shows a Brabender curve for an aqueous starch solution from the transgenic potato line JD1-71. The curve was determined as explained in Example 3.

The abbreviations are as defined for FIG. 3. The measurement conditions correspond to those described for FIG. 3.

Figure 6:
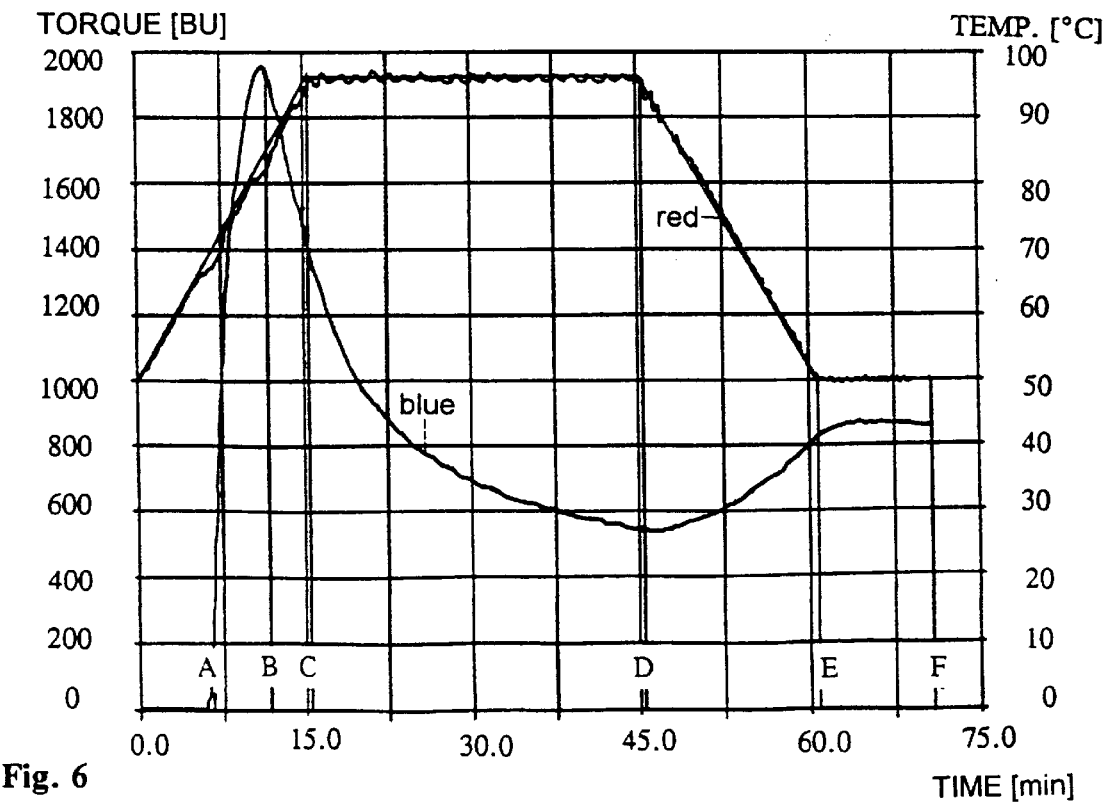

FIG. 6 shows a Brabender curve for an aqueous solution from starch of the wild-type plants *Solanum tuberosum* cf. Désirée. The curve was determined as explained in Example 3.

The abbreviations are as defined for FIG. 3. The measurement conditions correspond to those described for FIG. 3.

DETAILED DESCRIPTION OF THE INVENTION

The examples serve to illustrate the invention.
Media and Solutions Used

| | |
|---|---|
| 20 × SSC | 175.3 g NaCl |
| | 88.2 g sodium citrate |
| | ad 1000 ml with ddH$_2$O |
| | pH 7.0 with 10N NaOH |
| 10 × MEN | 200 mM MOPS |
| | 50 mM sodium citrate |
| | 10 mM EDTA |
| | pH 7.0 |
| NSEB buffer | 0.25M sodium phosphate buffer pH 7.2 |
| | 7% SDS |
| | 1 mM EDTA |
| | 1% BSA (w/v) |

Methods Used

1. Cloning Methods

For plant transformation, the gene constructs were cloned into the binary vectors BIN19 (Bevan Nucl. Acids Res. 12 (1984), 8711–8720) and pBinAR Hyg (DSM 9505).

2. Bacterial Strains

For the binary vectors, the *E. coli* strain DH5α (Bethesda Research Laboratories, Gaithersburg, USA) was used.

The transformation of the plasmids in the potato plants was carried out using the *Agrobacterium tumefaciens* strain C58C1 pGV2260 (Deblaere et al., Nucl. Acids Res. 13 (1985), 4777–4788).

3. Transformation of *Agrobacterium tumefaciens*

The transfer o the DNA was carried out by direct transformation according to the method by Höfgen & Willmitzer (Nucl. Acids Res. 16 (1988), 9877). The plasmid DNA of transformed Agrobacteria was isolated according to the method by Birnboim & Doly (Nucl. Acids Res. 7 (1979), 1513–1523) and was analyzed gel electrophoretidally after suitable restriction digestion.

4. Transformation of Potatoes

Ten small leaves of a potato sterile culture (*Solanum tuberosum* L.cv. Désirée) were wounded with a scalpel and placed in 10 ml MS medium (Murashige & Skoog, Physiol. Plant. 15 (1962), 473) containing 2% sucrose and 50 μl of a selectively grown overnight culture of *Agrobacterium tumefaciens*. After gently shaking the mixture for 3–5 minutes it was further incubated in the dark for 2 days. For callus induction, the leaves were placed on MS medium containing 1.6% glucose, 5 mg/l naphthyl acetic acid, 0.2 mg/l benzyl aminopurine, 250 mg/l claforan, 50 mg/l kanamycin or 1 mg/l hygromycin B and 0.80% Bacto Agar. After incubation at 25° C. and 3,000 lux for one week the leaves were placed for shoot induction on MS medium containing 1.6% glucose, 1.4 mg/l zeatin ribose, 20 mg/l naphthyl acetic acid, 20 mg/l giberellic acid, 250 mg/l claforan, 50 mg/l kanamycin or 3 mg/l hygromycin B and 0.80% Bacto Agar.

5. Radioactive Labeling of DNA Fragments

The DNA fragments were radioactively labeled using a DNA Random Primer Labelling Kit of Boehringer (Germany) according to the manufacturer's information.

6. Northern Blot Analysis

RNA was isolated from leave tissue of plants according to standard protocols. 50 μg of the RNA were separated on an agarose gel (1.5% agarose, 1×MEN buffer, 16.6% formaldehyde). The gel was shortly washed in water after the gel run. The RNA was transferred to a nylon membrane of the type Hybond N (Amersham, UK) using 20×SSC by means of capillary blot. The membrane was subsequently baked for 2 hours under vacuum at 80° C.

The membrane was prehybridized in NSEB buffer for 2 hours at 68° C. and subsequently hybridized in NSEB buffer overnight at 68° C. in the presence of the radioactively labeled probe.

7. Plant Maintenance

Potato plants were kept in the greenhouse under the following conditions:

Light time 16 hrs at 2500 lux and 22° C.
dark time 8 hrs at 150° C.
humidity 60%

8. Isolation of the Starch from Potato Plants

For the isolation of starch from potato tubers, the tubers were first crushed in a juicer. The resulting juice was mixed with low amounts of sodium sulfite and sodium bisulfite and was left to stand so that the starch could deposit. After deposition of the starch the supernatant was removed and the starch was washed at least 3 times in distilled water. Subsequently, the starch was dried at 37° C. by repeated tossing.

9. Determination of the Phosphate Content of the Starch

The phosphate content of the starch was determined by measuring the amount of phosphate bound to the C-6 position of glucose residues. For this purpose, starch was first hydrolyzed by acid hydrolysis and the content was then determined on glucose-6 phosphate via an enzyme test as described below:

100 mg starch were incubated for 4 hrs at 100° C. in 500 μl 0.7 N HCl. After acid hydrolysis, 10 ml of the mixture were added to 600 μl imidazole buffer (100 mM imidazole, 5 mM $MgCl_2$, pH 6.9; 2 mM $NADP^+$). The amount of glucose-6 phosphate in the mixture was determined by reaction with the enzyme glucose-6 phosphate dehydrogenase. For this purpose, 1 U of glucose-6 phosphate dehydrogenase (from yeast) was added to the mixture and the amount of NADPH formed was determined by measuring the absorbance at 340 nm.

EXAMPLE 1
Construction of the Binary Plasmid p35SH-anti-D

A copy of the coding region of the gene encoding the D enzyme was prepared from cDNA obtained from tuber tissue of *Solanum tuberosum* and using two synthetically produced oligonucleotides with the sequences 5'-GCCCCCGGGC TTTTAAGTTC CTTG-3' (Seq ID No. 1) and 5'-CAGGGTACCT AACATCTTAA TCATC-3' (Seq ID No. 2)

as primers for a polymerase chain reaction.

The resulting fragment comprises nucleotides 303 to 1777 of the nucleotide sequence shown in Takaha et al. (J. Biol. Chem. 268 (1993), 1391–1396). By way of the specific sequence of the oligonucleotides selected for amplification a Sma I restriction site is introduced at the 5' end of the codogenous strand and a Kpn I restriction site at the 3' end. The PCR fragment was digested with the restriction endonucleases Sma I and Kpn I and was ligated into the vector pBinAR-Hyg (DSM 9505) which had been digested with Sma I and Kpn I.

Figure 1:
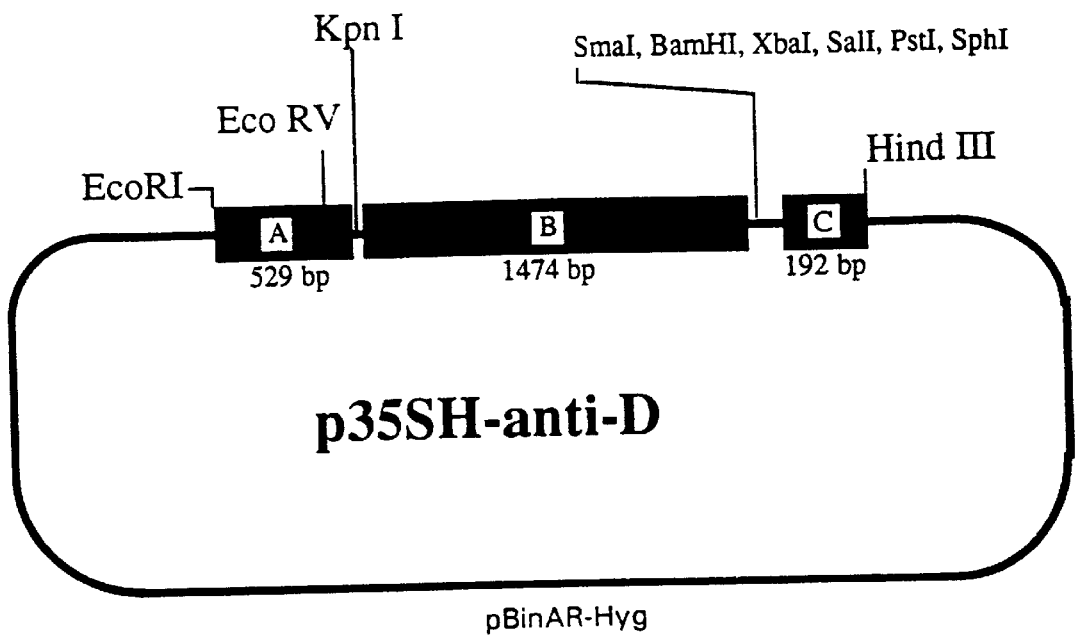
FIG. 1 shows plasmid p35SH-anti-D (DSM 8479).

The resulting plasmid was designated p35SH-anti-D (DSM 8479) and is shown in FIG. 1.

EXAMPLE 2
Construction of the Binary Plasmid p35S-anti-D

For the construction of plasmid p35S-anti-D, first plasmid pBIN19-AC was prepared. For this purpose, a 529 bp fragment comprising the 35S promoter of the CaMV (nucleotides 6909–7437, Franck et al., Cell 21, 285–294) from plasmid pDH51 (Pietrzak et al., Nucl. Acids Res. 14, 5857–5868) was isolated using restriction endonucleases EcoR I and Kpn I. This fragment was ligated into vector pBIN19 (Bevan, Nucl. Acids Res. 12 (1984), 8711–8721) which had been digested with EcoR I and Kpn I, resulting in plasmid pBIN19A.

Then a 192 bp fragment comprising the polyadenylation signal of gene 3 of the T-DNA of the Ti plasmid pTiACH5 (Gielen et al., EMBO J. 3, 835–846; nucleotides 11749–11939) was isolated as Pvu II/Hind III fragment from plasmid pAGV40 (Herrera-Estrella et al., Nature 303, 209–213). After addition of a Sph I linker to the Pvu II restriction site the fragment was ligated into vector pBIN19-A which had been digested with Sph I and Hind III. The resulting plasmid was designated pBIN19-AC.

For the construction of plasmid p35S-anti-D, the PCR fragment produced as described in Example 1 was ligated into vector pBIN19-AC which had been digested with Kpn I and Sma I.

The resulting plasmid is shown in FIG. 2.

EXAMPLE 3
Production of Transgenic Potato Plants with a Reduced D Enzyme Activity and Isolation of the Starch Synthesized in Said Plants For the production of transgenic potato plants in which the D enzyme activity is reduced as compared to wild-type plants, Agrobacteria of the species *Agrobacterium tumefaciens* were transformed with plasmid P35S-anti-D. The plasmid was transferred in cells of potato plants of the variety Désirée by Agrobacteria-mediated transformation as described above. From the transformed cells whole plants were regenerated. The transformed plants were cultivated under greenhouse conditions. The success of the genetic modification of the plants was assessed by analysis of the whole RNA in a Northern blot analysis with respect to the disappearance of the transcripts encoding the D enzyme. For this purpose, whole RNA from leaves of transformed plants were isolated according to standard techniques, separated on an agarose gel by gel electrophoresis, transferred to a nylon membrane and hybridized to a radioactively labeled probe comprising the region encoding the D enzyme from potato or a part of said region. In Northern blot analysis, successfully transformed plants lack the band representing the specific transcript of the D enzyme gene.

Four independent lines of transgenic potato plants, namely lines JD1-32, JD1-33, JD1-65 and JD1-71, in which only minor or no amounts of the D enzyme specific transcript could be detected by Northern blot analysis were examined more closely with respect to the starch they synthesize.

For this purpose, starch was isolated according to standard techniques from tubers from transgenic plants.

EXAMPLE 4
Analysis of the Starch from Potato Plants that were Transformed with Plasmid p35S-anti-D a) Determination of the Viscosity The starch isolated from the transgenic potato plants was examined with respect to the viscosity of aqueous solutions thereof.

In order to determine the viscosity of aqueous solutions of the starch synthesized in transformed potato plants 30 g each of starch were dissolved in 450 ml $H_2O$ and used for analysis in a Viskograph E (Brabender OHG Duisburg (Germany)). The apparatus was operated according to the manufacturer's recommendations. To determine the viscosity of the aqueous solution of starch the starch suspension was first heated from 50° C. to 96° C. at a rate of 3° C. per minute. Then, the temperature was maintained at 96° C. for 30 minutes. Afterwards, the solution was cooled from 96° C. to 50° C. at a rate of 3° C. per minute. During the entire time the suspension was stirred (75 revolutions per minute) and the viscosity was determined (in Brabender units). The results of such measurements are shown in form of curves in which the viscosity is depicted in dependence on time, in FIGS. 3, 4, 5 and 6. FIG. 3 shows a typical Brabender curve for starch, that of transgenic potato plants of the line JD1-32. FIG. 4 shows a typical Brabender curve for starch isolated from transgenic potato plants of the line JD1-33. FIG. 5 shows a typical Brabender curve for starch isolated from transgenic potato plants of the line JD1-71. FIG. 6 shows a typical Brabender curve for starch that was obtained from non-transformed potato plants of the variety Désirée. It is evident from these curves that in all three transgenic lines a starch is isolatable with almost identical viscosity properties. It is furthermore visible that the starch from transgenic potatoes displays properties that substantially differ from those of wild-type starch. From the curves shown various characteristic values can be derived.

For wild-type plants, the following characteristic values apply:

TABLE I

| Value | Name | time [min:sec] | torque [BU] | temperature [° C.] |
|---|---|---|---|---|
| A | start of pastification | 6:30 | 60.5 ± 17.7 | 69.9 ± 0.57 |
| B | maximum viscosity | 11:30 | 1838.0 ± 161.2 | 86.0 ± 2.1 |
| C | start of the holding time | 15:15 | 1412.0 ± 18.4 | 96.0 |
| D | start of the cooling time | 45:15 | 526.0 ± 17.0 | 96.0 |
| E | end of the cooling time | 60:30 | 812.0 ± 8.5 | 50.0 |
| F | end of the final holding time | 70:45 | 853.0 ± 5.7 | 50.0 |

Number of measurements n=2

Indicated are the mean values of the viscosity at different temperatures and at different points in time in Brabender units together with standard deviations, as well as the pastification temperature and the temperature at which maximum viscosity is reached.

For plants which had been transformed with plasmid p35S-anti-D, the following characteristic values apply:

TABLE II

Transgenic line JD1-32:

| Value | Name | time [min:sec] | torque [BU] | temperature [° C.] |
|---|---|---|---|---|
| A | start of pastification | 5:45 | 54.0 | 67.3 |
| B | maximum viscosity | 8:45 | 2905.0 | 76.3 |
| C | start of the holding time | 15:15 | 1459.0 | 96.0 |
| D | start of the cooling time | 45:15 | 631.0 | 96.0 |
| E | end of the cooling time | 60:30 | 986.0 | 50.0 |
| F | end of the final holding time | 70:45 | 1016.0 | 50.0 |

TABLE III

Transgenic line JD1-33:

| Value | Name | time [min:sec] | torque [BU] | temperature [° C.] |
|---|---|---|---|---|
| A | start of pastification | 5:45 | 16.0 | 67.3 |
| B | maximum viscosity | 9:30 | 2825.0 | 78.5 |
| C | start of the holding time | 15:15 | 1583.0 | 96.0 |
| D | start of the cooling time | 45:15 | 664.0 | 96.0 |
| E | end of the cooling time | 60:30 | 1019.0 | 50.0 |
| F | end of the final holding time | 70:45 | 1042.0 | 50.0 |

TABLE IV

Transgenic line JD1-71:

| Value | Name | time [min:sec] | torque [BU] | temperature [° C.] |
|---|---|---|---|---|
| A | start of pastification | 5:45 | 60.0 | 67.3 |
| B | maximum viscosity | 9:15 | 2741.0 | 77.8 |
| C | start of the holding time | 15:15 | 1510.0 | 96.0 |
| D | start of the cooling time | 45:15 | 629.0 | 96.0 |
| E | end of the cooling time | 60:30 | 989.0 | 50.0 |
| F | end of the final holding time | 70:45 | 1011.0 | 50.0 |

For the starch from transgenic potato plant in which the D enzyme activity is greatly reduced, following characteristic values can be determined under the above-mentioned test conditions:

a pastification temperature of 67.3±0.0° C., a maximum viscosity of 2823.7±82.0 BU, a viscosity at the start of the holding time of 1517.3±62.3 BU, a viscosity at the start of the cooling time of 641.3±19.7 BU, a viscosity after cooling down of 998.0±18.3 BU.

Considering measuring inaccuracies and deviations between the various transgenic lines with different D enzyme activities the mean values detected may deviate downwards or upwards by up to 10% so that the characteristic values for the modified starch may assume the following values:

a pastification temperature of 67.3±6.7° C., a maximum viscosity of 2824±283 BU a viscosity at the start of the holding time of 1517±152 BU a viscosity at the start of the cooling time of 641±65 BU a viscosity after cooling down of 998±100 BU.

Since the antisense technology allows to produce plants in which the expression of DNA sequences encoding D enzymes is inhibited to various degrees, the method according to the invention allows to produce transgenic plants displaying a more or less strong reduction of the D enzyme activity and therefore synthesizing a starch which differs more or less strongly from wild-type plants as regards its pastification properties.

b) Determination of the Phosphate Content

The determination of the phosphate content of starch from transgenic and from wild-type plants was carried out as described above.

The content in glucose-6 phosphate (indicated in nmol/mg starch) is indicated in the following table for non-transformed potato plants of the variety Désirée as well as mean value for three lines (JD1-32; JD1-65; JD1-71) of transgenic potato plants which had been transformed with plasmid p35S-anti-D.

TABLE V

| Plants | nMol glucose-6 phosphate/mg starch | % |
|---|---|---|
| Wild-type | 9.55 ± 0.62 | 100 |
| Transgenic lines | 12.80 ± 1.80 | 134 |

The values show that the phosphate content of the modified starch from transgenic potato plants is increased by about 34% as compared to starch from wild-type plants.

We claim:

1. A transgenic plant cell that exhibits a reduced D enzyme activity as compared to non-transformed cells and synthesizes a starch which is modified compared to starch from non-transformed cells in its physical and/or chemical properties, the reduction of the D enzyme activity being due to the presence of an exogenous DNA molecule the expression of which results in the inactivation of an endogenous D enzyme gene in the plant cell, resulting in an increase in the phosphate content of the starch synthesized in the cells, wherein the endogenous DNA molecule comprises a DNA sequence that is more than 80% homologous to the DNA sequence encoding potato D enzyme deposited in Deutsche Sammlung von Mikroorganismen (DSM) having deposit number DSM 8479 or DSM 9365.

2. The transgenic plant cell according to claim 1, which is a cell of a starch-storing plant.

3. The transgenic plant cell according to claim 2, wherein the starch-storing plant is a potato plant.

4. A transgenic plant comprising a plant cell according to any one of claims 1 to 3.

5. A propagation material of a plant comprising a plant cell according to any one of claims 1 to 3.

6. The propagation material according to claim 5, which is a seed or a tuber.

7. A method for producing a genetically engineered plant, wherein the plant synthesizes a modified starch having a phosphate content higher than that of naturally occurring starch, comprising the step of introducing into said plant an exogenous DNA molecule comprising a DNA sequence encoding a D enzyme, wherein the DNA sequence is more than 80% homologous to the DNA sequence encoding potato D enzyme deposited in Deutsche Sammlung von Mikroorganismen (DSM) having a deposit number DSM 8479 or DSM 9365.

8. The transgenic plant cell according to claim 1, wherein the exogenous DNA molecule composes a DNA sequence that is more than 90% homologous to the DNA sequence encoding the potato D enzyme deposited in Deutsche Sammlung von Mikroorganismen (DSM) having deposit number DSM 8479 or DSM 9365.

9. The transgenic plant cell according to claim 1, wherein the exogenous DNA molecule comprises a DNA sequence that is more than 95% homologous To the DNA sequence encoding the potato D enzyme deposited in Deutsche Sammlung von Mikroorganismen (DSM) having deposit number DSM 8479 or DSM 9365.

* * * * *